United States Patent [19]

Virnig

[11] Patent Number: 5,019,297
[45] Date of Patent: May 28, 1991

[54] PROCESS FOR ISOMERIZING OLEFINICALLY UNSATURATED SECONDARY ALCOHOLS

[75] Inventor: Michael J. Virnig, Santa Rosa, Calif.

[73] Assignee: Henkel Research Corporation, Santa Rosa, Calif.

[21] Appl. No.: 339,735

[22] Filed: Apr. 18, 1989

[51] Int. Cl.$^5$ ............................ C09F 7/08; C11L 3/14
[52] U.S. Cl. ............................... 260/405.6; 260/405.5; 568/341
[58] Field of Search ....................... 260/405.6

[56] References Cited

U.S. PATENT DOCUMENTS

| | | | |
|---|---|---|---|
| 2,178,760 | 11/1939 | Laxier | 260/411 |
| 2,340,745 | 2/1944 | Hanford | 260/405.6 |
| 2,847,432 | 8/1958 | Steadman et al. | 260/405.6 |
| 3,344,191 | 9/1967 | Chappell et al. | 568/341 |
| 4,301,084 | 11/1981 | Laas et al. | 260/405.6 |
| 4,310,709 | 1/1982 | Rebafka | 260/405.6 |
| 4,318,860 | 3/1982 | Hsu | 260/405.5 |
| 4,837,188 | 6/1989 | Laval et al. | 260/405.5 |

FOREIGN PATENT DOCUMENTS

| | | |
|---|---|---|
| 1156789 | 11/1963 | Fed. Rep. of Germany . |
| 635089 | 11/1978 | U.S.S.R. . |
| 566495 | 1/1945 | United Kingdom . |
| 2148892 | 6/1985 | United Kingdom . |

OTHER PUBLICATIONS

Journal of the American Oil Chemists Society, vol. 42, pp. 340–344 (1965).
Journal of Oil, Technologists Assoc. of the India, pp. 61–64 (Jul./Sep. 1976).

*Primary Examiner*—Paul J. Killos

[57] ABSTRACT

Olefinically unsaturated secondary alcohols in which the carbon-carbon double bond and the alcohol functionality are separated only by methylene groups are isomerized to ketones by reacting a mixture composed of an olefinically unsaturated secondary alcohol and a catalyst effective amount of a substantially fully hydrogenated palladium catalyst at a temperature of from about 200° C. to about 300° C. and passing hydrogen through the reaction mixture until the iodine number of said reaction mixture is less than 10 and separating the catalyst from the ketone.

9 Claims, No Drawings

PROCESS FOR ISOMERIZING OLEFINICALLY UNSATURATED SECONDARY ALCOHOLS

BACKGROUND OF THE INVENTION

1. Field of the Invention

This invention relates to a process for isomerizing olefinically unsaturated secondary alcohols to saturated ketones.

2. Description of the Related Art

A number of methods of isomerizing olefinically unsaturated secondary alcohols are known in the art. U.S. Pat. No. 2,178,760 discloses a process for catalytically isomerizing a hydroxy carboxylic acid or its functional derivative comprising heating the carboxylic acid or its functional derivative of a carboxylic acid in the presence of a nickel catalyst prepared by reducing an oxygen-containing nickel compound with hydrogen. U.S. Pat. No. 2,340,745 discloses a process for catalytically isomerizing a ricinoleic compound comprising heating a ricinoleic compound in the presence of an elementary nickel or cobalt catalyst. U.S. Pat. No. 2,847,432 discloses a method of oxidizing an alkyl ester of 12-ketostearic acid comprising reacting the ester with nitric acid in the presence of a mixed catalyst containing a copper tearing material. Japanese Kokai 73 48,417 (Chemical Abstracts 79:125878e) discloses the isomerization of unsaturated hydroxy fatty acids and their esters by heating the unsaturated hydroxy fatty acids and their esters in the presence of copper, nickel, or palladium. The Journal of the American Oil Chemists Society Vol 42, pages 340-344 1965) describes a method of preparing methyl 12-ketostearate by heating methyl ricinoleate over Raney nickel catalyst for about one-half hour. The Journal of Oil Technologists' Association of India, pages 61–64July/September 1976 describes the production of keto stearic acids through the hydrogenation of castor oil in the presence of Raney Nickel. Maslobiona Zhirovoa Delo. 13, (2) 13–14 (1937) (Chemical Abstracts 31, 7397) describes a method of preparing 12-ketostearic acid by heating castor oil in a $CO_2$ atmosphere in the presence of nickel, copper, and platinum black catalysts. The preparation of 12-ketostearic acid by isomerizing methyl ricinoleate over raney nickel is described in Bull. Soc. Chim. France, pages 339–42 (1954) (Chemical Abstracts 49, 4520 c). French patent No. 1,043,797 (Chemical Abstracts 52, 11908 b) discloses a method of preparing methyl 12-oxostearate by reducing methyl ricinoleate with hydrogen over a Cu-$ZrO_2$ catalyst.

None of the prior art methods discloses a substantially fully hydrogenated catalyst. All of prior art methods suffer from the disadvantage that a substantial amount of the saturated hydroxy compound or the unsaturated keto compound is formed along with the desired saturated keto compound.

SUMMARY OF THE INVENTION

The process of the present invention overcomes the above difficulties by producing keto compounds that contain low levels of the saturated hydroxy compound or the unsaturated keto compound. It is therefore, an object of the present invention to provide a process for isomerizing olefinically unsaturated secondary alcohols wherein the carbon-carbon double bond and the alcohol functionality of the secondary alcohols are separated only by methylene groups comprising the steps of: (1) reacting said olefinically unsaturated secondary alcohol in the presence of a catalyst effective amount of a substantially fully hydrogenated palladium catalyst at a temperature of from about 200° C. to about 300° C. to produce a reaction mixture, (2) passing hydrogen through said reaction mixture until the iodine number of said reaction mixture is less than about 10 to produce a saturated ketone, and (3) separating said catalyst from said ketone.

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about".

The present invention provides a general method of preparing ketones with a minimum amount of the saturated alcohol formation or the unsaturated keto compound formation by isomerizing olefinically unsaturated secondary alcohols in which the carbon-carbon double bond and the alcohol functionality are separated only by methylene groups in the presence of a fully hydrogenated palladium catalyst and hydrogen. The process of the present invention is generally carried out by first vigorously stirring a reaction mixture of olefinically unsaturated secondary alcohol and catalyst heated to 250° C. under a nitrogen atmosphere for 1 to 2 hours. At the end of the 2 hour period, a trickle of hydrogen is introduced from a glass frit under the liquid reaction mixture surface while maintaining the temperature at 250° C. The passage of hydrogen through the reaction mixture is continued until the reaction has been completed as indicated by reduction in the iodine number of the reaction mixture to a value of 10 or preferably below 10. The reaction mixture is then cooled to room temperature and the catalyst is separated from the reaction product usually by filtration. The catalyst can be reused many times in subsequent reactions.

It is essential that the palladium catalyst be substantially fully hydrogenated in order that any of the corresponding saturated alcohol and/or unsaturated ketone formed in the reaction be kept to a minimum. For purposes of this invention, a substantially fully hydrogenated catalyst is a catalyst that has been fully saturated with hydrogen. The catalyst may be made substantially fully hydrogenated by dispersing it as received in an inert solvent such as a liquid paraffin and passing gaseous hydrogen through the catalyst-solvent dispersion for about 2 hours at temperatures from room temperature to 200 deg. C. A preferred method of substantially fully hydrogenating the catalyst of the present invention is by taking a 5% palladium-on-carbon catalyst as received from the manufacturer and using it in the process of the present invention. The catalyst is then substantially fully hydrogenated and can be recycled repeatedly in the process. Any finely divided form of elemental palladium can be used in the process of the present invention. It is preferred that the palladium be deposited on inert carrier in an amount equal to about 5% by weight of palladium based on the total weight of the palladium/inert carrier weight. In order to minimize the formation of the saturated hydroxy compound or the unsaturated keto compound in the process of the present invention, it is most preferred that the catalyst be sulfided 5% palladium-on-carbon. Sulfided 5% palladium-on-carbon catalyst is available commercially (sold as palladium on sulfide carbon by Aldrich Chemical Co.)

The amount of catalyst that is required in the process of the present invention is any amount that is necessary to complete the conversion of olefinically unsaturated alcohol to a ketone in a reasonable period of time such as 3 to 6 hours. The preferred amount of catalyst is in the range of 0.5% to 10% by weight of olefinically unsaturated secondary alcohol. The most preferred amount of catalyst is 2.5% by weight of olefinically unsaturated secondary alcohol.

Any olefinically unsaturated secondary alcohol in which the alcohol and carbon-carbon double bond are separated only by methylene groups can be isomerized by the process of the present invention. Examples of such alcohols include but are not limited to 3-buten-2-ol, 1-penten-3-ol, 3-penten-2-ol, 2-cyclohexen-1-ol, 1-hexen-3-ol, 1-octen-3-ol. The unsaturated secondary alcohol moiety can also be part of a molecule that contains other functional groups as is the case of simple alkyl esters of ricinoleic acid (12-hydroxy-9,10-octadecenoic acid) such as the $C_1$–$C_6$ alkyl esters of ricinoleic acid or castor oil, a triglyceride whose fatty acid content is high (87%) in ricinoleic acid. Since the process of the present invention is particularly applicable to the isomerization of castor oil the most preferred unsaturated secondary alcohol is castor oil.

The process of the present invention can be carried out at any temperature between 200° C. and 300° C. The most preferred temperature is 250° C.

The process of the present invention can be carried out in the presence of an inert solvent such as a liquid paraffin. The process of the present invention is not limited to being carried out at atmospheric pressure. Obviously, the isomerization of low molecular weight alcohols such as 3-buten-2-ol whose boiling point is about 96° C. or 1-penten-3-ol whose boiling point is about 114° C. would have to be carried out at pressures greater than 1 atmosphere. It would be very advantageous both from a cost and safety standpoint to carry out the process involving any alcohol which can be used in the process of the present invention in a closed pressure vessel at a pressure above atmospheric pressure while recycling the hydrogen through the reaction mixture until the reaction has been completed as indicated by the reduction in the iodine number to a value below 10. It is preferred that the process of the present invention be carried out above atmospheric pressure.

The following examples are meant to illustrate but not limit the invention.

EXAMPLE 1

Isomerization of Castor Oil

Into a 3-neck morton flask equipped with a thermometer, a glass paddle stirrer, a condenser, and a glass frit for gas introduction were placed 150 grams of castor oil and 15 grams of substantially fully hydrogenated 5% palladium-on-carbon. The contents of the flask were heated with stirring to 250° C. while nitrogen was constantly swept through the flask. After the temperature reached 250° C., 450 grams of additional castor oil were added over a period of 1 hour. After the addition was finished, the reaction mixture was stirred vigorously at 250° C. for 2 hours after which a trickle of hydrogen was introduced into the reaction mixture from the glass frit and continued with vigorous agitation for about 1 hour. The reaction mixture was cooled to room temperature and the catalyst separated by filtration to yield 595 grams of isomerized castor oil. The fatty acid distribution of the starting material and the final product are given in Table 1.

TABLE 1

| Fatty Acid Distribution of Starting Material and Final Product[1] | | |
|---|---|---|
| Fatty Acid | Starting Material | Product |
| palmitic | 1.0 | 1.2 |
| oleic | 3.7 | 0.0 |
| stearic | 3.4 | 12.5 |
| ricinoleic | 89.0 | 0.0 |
| 12-ketostearic | 0.0 | 73.5 |
| 12-hydroxystearic | 0.0 | 10.4 |

[1]area % of methyl esters by GLC analysis.

EXAMPLE 2

Isomerization of Castor Oil using recycled catalyst

The procedure of Example 1 was repeated at a smaller scale, initially placing 60 grams of castor oil and 6.25 grams of 5% palladium-on-carbon (dry weight) that had been recovered from a previous isomerization experiment. After the well-stirred mixture reached 250° C., 190 grams of additional castor oil was added over a period of 1 hour. After vigorously stirring for an additional 2 hours at 250° C., a trickle of hydrogen was introduced into the reaction mixture for 2 hours. The reaction mixture was cooled and the catalyst separated by filtration to yield 247.6 grams of isomerized castor oil. The fatty acid distribution of the final product is given in Table 2.

EXAMPLE 3

Isomerization of Castor Oil using recycled sulfidized catalyst

The procedure of Example 2 was repeated using recovered 5% palladium on sulfided carbon (Engelhard) which had been substantially fully hydrogenated in a previous isomerization experiment. The experiment yielded 249.6 gm of isomerized castor oil, the fatty acid distribution of which is given in Table 2. This shows that the use of sulfidized catalyst results in significantly reduced levels of 12-hydroxystearic acid, and higher levels of 12-ketostearic acid.

TABLE 2

| Fatty Acid Distribution of Isomerized Product[1] | | |
|---|---|---|
| Fatty Acid | Example 2 | Example 3 |
| palmitic | 1.5 | 1.4 |
| oleic | 0.0 | 0.0 |
| stearic | 12.6 | 17.1 |
| ricinoleic | 0.0 | 0.0 |
| 12-ketostearic | 75.8 | 78.4 |
| 12-hydroxystearic | 7.4 | 2.6 |

[1]area % of methyl esters by GLC analysis.

EXAMPLE 4

Isomerization of Castor Oil; comparison of unreduced catalyst versus catalyst reduced by recycling The procedure of Example 2 was repeated using an initial charge of 110 grams castor oil and 18.2 grams (dry weight) of 5% palladium on carbon—unreduced (Heraeus K-0201). After the well-stirred mixture reached 250 deg. C., 255 grams of additional castor oil was added over 1 hour. After vigorously stirring for an additional 2 hours, a trickle of hydrogen was introduced into the reaction mixture for 2 hours. The catalyst was then removed by filtration. The fatty acid distribution of the final product is given in Table 3.

Half of the recovered catalyst was used in a recycle experiment. The initial charge of castor oil was 113 grams, followed by the addition of 262 grams castor oil over 1 hour. Other conditions were the same. The fatty acid distribution of the final product is given in Table 3.

TABLE 3

| Fatty Acid Distribution of Isomerized Product[1] | | |
|---|---|---|
| Fatty Acid | Unreduced Catalyst | Recycled Catalyst |
| oleic | 3.1 | 0.0 |
| stearic | 25.2 | 13.7 |
| ricinoleic | 0.0 | 0.0 |
| 12-ketostearic | 60.6 | 74.9 |
| 12-OH stearic | 6.6 | 8.5 |

[1] area % of methyl esters by GLC analysis.

What is claimed is:

1. A process for isomerizing an olefinically unsaturated secondary alcohol wherein the carbon-carbon double bond and the alcohol functionality of said secondary alcohol are separated only by methylene groups which comprises: (1) reacting said olefinically unsaturated secondary alcohol in the presence of a catalyst effective amount of a substantially fully hydrogenated palladium catalyst at a temperature of from about 200° C. to about 300° C. to produce a reaction mixture, (2) passing hydrogen through said reaction mixture until the iodine number of said reaction mixture is less than about 10 to produce a saturated ketone, and (3) separating said catalyst from said ketone.

2. The process of claim 1 wherein said catalyst is selected from the group consisting of 5% palladium-on-carbon and sulfided 5% palladium-on-carbon.

3. The process of claim 1 wherein said catalyst is sulfided 5% palladium-on-carbon.

4. The process of claim 2 wherein the amount of said catalyst is equal to from about 0.5% to about 10% by weight of said olefinically unsaturated secondary alcohol.

5. The process of claim 4 wherein the amount of said catalyst is equal to about 2.5% by weight of said olefinically unsaturated secondary alcohol.

6. The process of claim 1 wherein said olefinically unsaturated secondary alcohol is castor oil.

7. The process of claim 1 wherein said olefinically unsaturated secondary alcohol is a $C_1$–$C_6$ alkyl ester of ricinoleic acid.

8. The process of claim 1 wherein said reacting in step (a) is carried out for a period of from about 1 to about 2 hours.

9. The process of claim 1 wherein said process is carried out above atmospheric pressure.

* * * * *